United States Patent [19] [11] Patent Number: 4,605,623
Malette et al. [45] Date of Patent: Aug. 12, 1986

[54] METHOD OF ALTERING GROWTH AND DEVELOPMENT AND SUPPRESSING CONTAMINATION MICROORGANISMS IN CELL OR TISSUE CULTURE

[76] Inventors: William G. Malette, 667 Parkwood La., Omaha, Nebr. 68132; Herbert J. Quigley, Jr., 9511 Mockingbird Dr., Omaha, Nebr. 68127

[21] Appl. No.: 522,974

[22] Filed: Aug. 15, 1983

Related U.S. Application Data

[63] Continuation-in-part of Ser. No. 440,039, Nov. 8, 1982, Pat. No. 4,532,134.

[51] Int. Cl.$^4$ .................. C12N 5/00; C12N 5/02; C12R 1/91; A61K 30/12
[52] U.S. Cl. .................... 435/240; 435/241; 435/948; 424/95; 514/55
[58] Field of Search .............. 435/240, 241, 948, 177, 435/178, 174, 176, 180; 424/180, 95; 423/413

[56] References Cited

U.S. PATENT DOCUMENTS

| 3,903,268 | 9/1975 | Balassa | 424/180 |
| 3,914,413 | 10/1975 | Balassa | 424/180 |
| 4,352,134 | 9/1982 | Malette et al. | 514/55 |
| 4,394,373 | 7/1983 | Malette et al. | 424/95 |

FOREIGN PATENT DOCUMENTS

82/00660 3/1982 PCT Int'l Appl. .............. 435/178

Primary Examiner—Thomas G. Wiseman
Assistant Examiner—Robin Lyn Teskin
Attorney, Agent, or Firm—Zarley, McKee, Thomte, Voorhees & Sease

[57] ABSTRACT

A method for cultivating myocytes in suspension using water soluble chitosan is taught. The method results in the three-dimensional growth of the cultured myocytes as well as the inhibition of certain undesired cells.

12 Claims, No Drawings

METHOD OF ALTERING GROWTH AND DEVELOPMENT AND SUPPRESSING CONTAMINATION MICROORGANISMS IN CELL OR TISSUE CULTURE

BACKGROUND OF THE INVENTION

This is a continuation-in-part of our co-pending application, Ser. No. 440,039, now allowed U.S. Pat. No. 4,532,134 filed Nov. 8, 1982.

In applicants' earlier application, a method was described for inhibiting fibroplasia and promoting tissue growth and differentiation in a tissue wound. Since the filing of the co-pending application, the inventors have discovered that chitosan may be used to inhibit fibroplasia and to promote tissue growth and differentiation in tissue culture.

Cell culture or tissue culture has been used for years to study growth patterns of undifferentiated neoplasms and for basic research in cellular metabolism. Recently, large-scale cell culture preparations have been used to produce pharmaceutical materials. Methods to stimulate the growth and/or differentiation of such cell cultures would affect the yield and/or composition of these biological products. Most tissue cultures grow in monolayers on the bottom or sides of vessels in a two-dimensional architecture or as cells growing individually suspended in media. Three-dimensional tissue culture has been reported in collagen (protein) gels. Multiplication of complex cells in three dimensions raises the possibility of growing tissues for transplantation.

Microorganisms, particularly bacteria and mycoplasma, can flourish in cell culture media. High levels of potent antibiotics are routinely used prophylactically to inhibit contamination of the cultures. The antibiotics may interfere with the growth and development of the tissue being studied. In many instances, grossly contaminated cell cultures must be discarded, with a significant loss of time and materials.

Therefore, it is a principal object of this invention to describe a method of treating tissue cultures or cell cultures so as to increase, selectively decrease, or alter the growth and differentiation of particular cells.

Still another object of the invention is to provide a method of treating the culture vessel or the media to support three-dimensional tissue growth in a non-protein matrix.

Still another object of the invention is to provide a method of suppressing contamination of cell cultures by microorganisms.

These and other objects will be apparent to those skilled in the art.

SUMMARY OF THE INVENTION

A method of altering the growth and/or development of tissue cultures is described comprising the steps of: (1) providing a non-protein matrix for three-dimensional tissue growth, and (2) preventing or suppressing contamination of microorganisms by placing chitosan or chitosan derivatives in contact with the cell culture. Chitosan employed in this invention is approximately 45% to 100% de-acetylated having a molecular weight of 10,000 to 2,055,000. The chitosan may be in solution or solid form.

DESCRIPTION OF THE PREFERRED METHOD

In our previous work with chitosan in hemostasis and growth and differentiation of tissue in vivo, we observed rapid growth of undifferentiated cells into the chitosan layer around vascular grafts. Surprisingly, the cells developed into smooth muscle rather than the expected collagen fibrous tissue. We decided to investigate the effect of chitosan on cell growth and differentiation in tissue culture. We had access to a functional, standard cell culture preparation for the growth of cardiac muscle cells by the method of Yaffe [Yaffe, D., Rat skeletal muscle cells. in "Tissue Culture, Methods and Applications", edited by Kruse and Patterson, Academic Press (1973) pp. 106-114]. It was with this tissue culture preparation and sterile chitosan hemostatic solution (prepared according to the method in U.S. Pat. No. 4,394,373 and pending application Serial No. 440,039, now allowed U.S. Pat. No. 4,352,134 which are made a part hereof) that the experiments began.

EXPERIMENT I

Neonatal Sprague Dawley rats were used. The heads were removed with sterile scissors and the bodies were immersed in 70% ethanol. With sterile scissors, the hearts were removed and placed in a tube containing 90.8 ml of calcium and magnesium free, phosphate buffered saline (PBS-CMF); 5 ml of fetal bovine serum (FBS); 2 ml of a solution containing 10,000 units of penicillin and 10,000 mcg of streptomycin per ml (PS); 2 ml of amphotericin B, 250 mcg per ml (AB); and 0.2 ml of a solution containing 10 mg/ml of gentamycin (GNT). The neonatal hearts were carried from the animal room to the tissue culture laboratory in the antibiotic solution at room temperature. Within 30 minutes of sacrifice, the hearts were transferred to 10 ml sterile petri dishes containing (PBS-CMF) and rinsed twice with fresh solution. The hearts were held by the atria, and the ventricles were sliced into tiny pieces, then chopped finely with sterile blades. Ten ml of the minced ventricular muscle was placed in a conical tube containing 45 ml of PBS-CMF plus 5 ml of 2.5% trypsin solution. The suspensions were incubated for 2 hours at 37° C. on a rotational mixer at 100 RPMs. To each tube 16 ml of Dulbecco's Modified Eagle Medium (DMEM) and 4 ml of FBS was added. The suspension was thoroughly mixed, and the tubes were placed in an upright position. Five ml of FBS was carefully layered on the bottom of the tube, and the debris was permitted to sediment for 10 minutes. The cell suspension above the debris layer was carefully removed and centrifuged at 1500 RPM for 10 minutes. The cell pellets were resuspended in 87.8% DMEM, 10% FBS, 1% PS, 1% AB, and 0.2% GNT and plated out in 10 ml culture dishes for 2 hours. Most of the unwanted fibroblasts firmly attached to this first culture plate, leaving the myocytes in suspension. The concentration of cells was then determined, and suspensions containing one million cells per 35 mm culture dish were plated. The plates were incubated at 37° C. with 5% carbon dioxide enriched air. The old media was decanted; and fresh feeding media was added on the second day following plating, and then every two days thereafter. The feeding media for controls was a mixture of 87.8 ml of DMEM, 10 ml of FBS, 1 ml of PS, 1 ml of AB, and 0.2 ml of GNT. The growth and development of rat cardiac muscle in this system in our laboratory was determined in over 100 platings (for other experiments). Most myocytes lie down between 24 and 48 hours following plating. Between 4 and 5 days, myotubes start to form around the edges of the plates. Contraction centers form between 7 and 10 days. The plate is covered by growth in 14 days. Uniform contraction over the surface of the plate starts at 15 days.

For our first experiment with chitosan, myocytes were plated in the usual manner. The feeding solution was modified by the addition of 10 ml of preferred chitosan hemostatic solution (containing 2 mg/ml chitosan flakes or powder in 0.026 N acetic acid) to 90 ml of the feeding solution described above. Each 35 mm plate required about 5 ml of fresh solution at each feeding. After one day, a layer of chitosan covering the myocytes on the bottom of the plate is clearly discernable. Chitosan sticks to the plate and to the myocytes, so that the old chitosan is incompletely decanted with feeding solution change. The concentration of chitosan on the plate increases with each solution change. Observation of 20 plates treated with chitosan revealed that myotubes formed in 2 to 3 days. Contraction centers formed between 4 and 5 days. The plates were covered with growth in 9 days. Uniform contraction of the surface started at 10 days. The most remarkable observation was that individual myoctyes would raise up into the chitosan layer from dividing cells with glass contact, and continue to grow and divide. By 14 days some foci on the plate had a definite three-dimensional growth pattern. The layered cells beat in unison with the cells underneath as functional, three-dimensional cardiac tissue. In the control plates we frequently observed individual cells that were squeezed from surface contact by adjacent growth. They would assume a spherical shape in the feeding solution, and would not grow or function without surface contact. Chitosan fibers in the media apparently provided satisfactory "surface" contact to induce the myocytes to continue to grow and function. Such a chitosan surface could be applied to the bottom and sides, or to beads suspended in solution, to increase the surface-contact growing layer in a vessel.

EXPERIMENT II

The preparation of control and chitosan treated cultures was repeated with split samples of the same cell suspension to guarantee that observed differences in growth rate and development were not the result of different numbers of cells on chitosan versus control plates. We had previously observed that rat cardiac myocytes grew more rapidly in higher cell densities. The controlled study (20 plates each) yielded similar results, confirming the faster growth and development of the chitosan treated cultures. We again observed the true "tissue" growth in three dimensions.

EXPERIMENT III

Changes in concentration were tried. The addition of a feeding solution that was 50% chitosan hemostatic solution plus 50% normal feeding solution (100 mg chitosan per 100 ml feeding solution) yielded slower than normal growth and development under a thick chitosan gel layer. Three-dimensional growth did occur in plates that were maintained for 30 days. Fibroblasts did not grow in this concentration. Feeding solutions containing 10 mg and 5 mg of chitosan per 100 ml showed increased rates of growth and development with chitosan fibers sticking to the myocyte surfaces by electron microscopy; however, three-dimensional growth was less pronounced.

EXPERIMENT IV

In eight cultures, 45% deacetylated chitosan solution yielded a thick, well-defined gel layer when mixed with feeding solution; however, cell growth was retarded compared to the controls. Low average molecular weight (low viscosity) 100% deacetylated polyglucosamine did stick to the myocytes in 20 mg/ml concentration, but most remained in suspension in the fluid as chitosan particles which did not form a definitive gel layer. Rate of growth and development was enhanced by polyglucosamine, but three-dimensional growth was less prominent in seven cultures.

EXPERIMENT V

Pure cultures of human fibroblasts were obtained. The addition of chitosan hemostatic solution in a concentration of 20 mg per 100 ml of feeding solution yielded more rapid growth than normal feeding solution. A three-dimensional growth pattern with fibroblasts actually interlacing perpendicular to each other developed, yielding a woven mat of fibroblasts. Higher concentrations of chitosan in feeding solution inhibited fibroblast growth. Mixed cultures of rat fibroblasts and rat myocytes revealed that a concentration of 30 mg per 100 ml of feeding solution permitted myocyte growth to continue while inhibiting fibroblasts. Plates were ultimately covered by 95% myocytes and 5 fibroblasts.

EXPERIMENT VI

Eight plates were pretreated with 5 ml of a 20 mg per 100 ml chitosan feeding solution to develop a gel layer which coated the surface of the plate. Myocytes added to this chitosan gel were slower to lie down; however, the cell division and cell multiplication rate were greatly increased. This study of pretreating the plates was continued by adding 5 ml of preferred chitosan acetate solution to plates and letting them evaporate to dryness in a dessicator. The bottom and sides of the plates were found to be coated by a thin transparent film of dry chitosan acetate. Myocytes in standard cell suspension (no chitosan) were placed on these plates and control plates. At 16 hours, 25% of the control myocytes had lain down and begun to change their shape, as usual about 10% of these were dividing. On the chitosan coated plates only 10% of the cells had lain down, however, 90% of these myocytes were dividing. By the third day, rapid cell division had produced a heaped up layer of myocytes at the junction of the chitosan and feeding solution. Some cells that were slightly elongate (three times as long as wide) started beating. By the sixth day (after two changes of feeding solution) most of the film had washed off; however, islands of piled-up, beating myocytes remained on the foci of chitosan that still adhered to the plate. The application of mixed cultures of 50rat myocytes and 50% rat fibroblasts to chitosan coated plates revealed that 10% of the myocytes lay down in 16 hours; however, none of the fibroblasts had lain down. This was vastly different from the control mixed cell cultures in which the fibroblasts lay down much faster than myocytes and blocked the myocytes from reaching the surface. By the sixth day, islands of beating myocytes remained on the plates. The fibroblasts had died and/or had been washed off the plates with the changed feeding solution.

EXPERIMENT VII

Plates covered with freeze-dried chitosan acetate fibers showed similar ability to accept plating of cells and stimulate rapid growth. Prewetting with feeding solution resulted in faster laying down and greater survival of cells than was experienced in attempts to pour the cell suspensions directly on the solid chitosan fibers. Dialysing the chitosan against several changes of feeding solution before precoating the plates improved the survival of cells from plated suspensions.

EXPERIMENT VIII

At irregular intervals, but more commonly in the Spring, cultures of rat pup tissues are contaminated de novo with mycoplasma that flourish in the presence of the penicillin, streptomycin, amphoteracin B, and gentamycin in the standard media. Such tissue cultures are usually discarded. Several female breeding rats have had to be destroyed due to chronic mycoplasma infections which were spread to their progeny. While performing Experiment II, several plates were found to show intense movement of the media under the microscope due to gross contamination which mycoplasma two days after plating, (just before the first change of feeding solution). Despite the presence of microorganisms, the fluid was decanted and the chitosan containing feeding solution was added to the contaminated plates. As observed through the microscope, all motion ceased in the chitosan fed plates. The muscle cells grew and developed as expected over the next 30 days without recurrence of detectable mycoplasma infestation. A parallel series of twenty-four plates deliberately plated with contaminated fetal tissue were confirmed to contain gross contamination by mycoplasma two days following plating. Half were fed solution containing 20 mg chitosan per 100 ml. The contaminated plates fed the standard quadruple antibiotic solution revealed death of the myocytes; while the chitosan fed plates grew and developed similar to non-contaminated, chitosan treated tissue cultures.

EXPERIMENT IX

A series of eight plates was found to be contaminated with mycoplasma and bacteria two days after plating. Treating four of the plates with solution containing 20 mg/100 ml chitosan permitted normal growth and development. The myocytes on the four untreated plates died in the cloudy media.

EXPERIMENT X

We obtained two other contaminating mycoplasma from an investigator at another institute. One organism was contaminating neonatal bovine tissue and the other was contaminating neonatal canine tissue. The canine mycoplasma grew well in our standard feeding solution and destroyed control cultures. The bovine mycoplasma was inhibited and multiplied slowly in our control cultures fed standard feeding solution. In each case addition of chitosan to the feeding solution caused the mycoplasma to disappear and permitted normal growth and development of the tissue cultures. In a standard clinical microbiology laboratory, we were able to grow the mycoplasma on PPLO media and to determine that the organisms were not M. hominis, M. pneumoniae, nor U. urealyticum. We have therefore referred to them as Mycoplasma species with source of origin from rat, dog or cow.

The conclusions reached by studying Experiments I-X hereinabove are that the chitosan of this invention does alter the growth and development of cell cultures, does provide a non-protein matrix for three-dimensional tissue growth, and does suppress contamination by microorganisms in tissue culture. Thus it can be seen that the method of this invention accomplishes at least all of its stated objectives.

We claim:

1. A method for cultivating myocytes in suspension comprising growing myocytes in a culture media containing an amount of an aqueous chitosan solution sufficient to enable the three-dimensional growth of said myocytes and to inhibit certain undesired cells in the culture media including fibroblasts, tumor cells, mycoplasma and bacteria, wherein the source of chitosan is a chitosan derivative selected from polyglucosamine or chitosan salts which are essentially water soluble at ambient temperature.

2. The method of claim 1 wherein said chitosan derivative is dissolved in the media and is an ingredient of the liquid media.

3. The method of claim 3 wherein said chitosan derivative is in solid form.

4. The method of claim 2 wherein said chitosan derivative is applied to the culture vessel before the media or cells are applied to the vessel.

5. The method of claim 4 wherein said chitosan derivative is a film.

6. The method of claim 4 whereinsaid chitosan derivative is a sheet.

7. The method of claim 4 wherein said chitosan derivative is in fiber form.

8. The method of claim 4 wherein said chitosan derivative is a powder.

9. The method of claim 6 wherein said fibers are formed into mats.

10. The method of claim 1 wherein said chitosan derivative is incorporated into the feeding solution and added fresh each time the old media is decanted or aspirated.

11. The method of claim 1 wherein said chitosan derivative comprises deacetylated chitin having a molecular weight of 10,000 to 2,055,000.

12. The method of claim 11 wherein said chitosan derivative is 45% to 100% deacetylated.

* * * * *